United States Patent [19]

Fuller et al.

[11] Patent Number: 5,998,185
[45] Date of Patent: Dec. 7, 1999

[54] SILICONE RUBBER FOAM SUPPORT STRUCTURES FOR IMMOBILIZATION OF CELLS

[75] Inventors: Jess Paul Fuller; Tony Clayson, both of Ashby-de-la-Zouch; Anthony James Knights, Swansea, all of United Kingdom

[73] Assignee: Ashby Scientific, Ltd., Leicestershire, United Kingdom

[21] Appl. No.: 08/495,422

[22] PCT Filed: Dec. 23, 1993

[86] PCT No.: PCT/GB93/02644

§ 371 Date: Aug. 24, 1995

§ 102(e) Date: Aug. 24, 1995

[87] PCT Pub. No.: WO94/16058

PCT Pub. Date: Jul. 21, 1994

[30] Foreign Application Priority Data

Dec. 31, 1992 [GB] United Kingdom .................... 9227134

[51] Int. Cl.[6] .............................. C12N 11/08; C12N 5/00; C12P 1/00; C02F 3/00
[52] U.S. Cl. ........................... 435/180; 210/601; 435/41; 435/70.1; 435/71.1; 435/161; 435/182; 435/395; 435/262.5
[58] Field of Search .............................. 435/41, 174, 177, 435/180, 182, 249.23, 262.5, 70.1, 71.1, 161, 395; 210/601

[56] References Cited

U.S. PATENT DOCUMENTS 5,079,011  1/1992  Lommi et al. ............................ 426/11
5,190,872  3/1993  Hashizume et al. .................... 435/174
5,266,476  11/1993  Sussman et al. .................. 435/240.23

FOREIGN PATENT DOCUMENTS 2522014  8/1983  France .

OTHER PUBLICATIONS

Derwent Abstract, 88–268198, Mar. 28, 1994.
Sheldon W. May and Raymond E. Spier, Enzyme and Microbial Technology, vol. 10, No. 9, Sep. 1988, Haywards Heath, England.
Jennifer Van Brunt, Immobilized Mammalian Cells: The Gentle Way To Productivity, vol. 4, No. 6, Jun. 1986.

*Primary Examiner*—David M. Naff
*Attorney, Agent, or Firm*—Wolf, Greenfield & Sacks, PC

[57] ABSTRACT

Resilient openly porous support structures containing silicon are prepared for cell immobilization. A preferred structure is made of porous silicone rubber foam, and cells are adsorbed to the surfaces of pores. The structure may be in the form of a block, sheet, pad, chip, strand, tube or granule. The silicone rubber foam is formed by aerating liquid silicone rubber, and desired porosity and density are provided by controlling aeration of the liquid silicone rubber. The porosity and/or density may also be controlled by incorporating during manufacture of the structure an inert additive such as a metal powder that produces a dense structure. A density may be provided to prevent the structure from floating in a reaction mixture in which the structure is used. Additives may also be used to control surface properties of the structure. The structure is preferably sterilized before use and may be re-used. The structure is re-used without removing cells or is cleaned to remove cells and then re-sterilized. After loading with a culture of cells or cultures of different cells, the structure is added to a reaction medium in a bioreactor to produce a product.

33 Claims, 1 Drawing Sheet

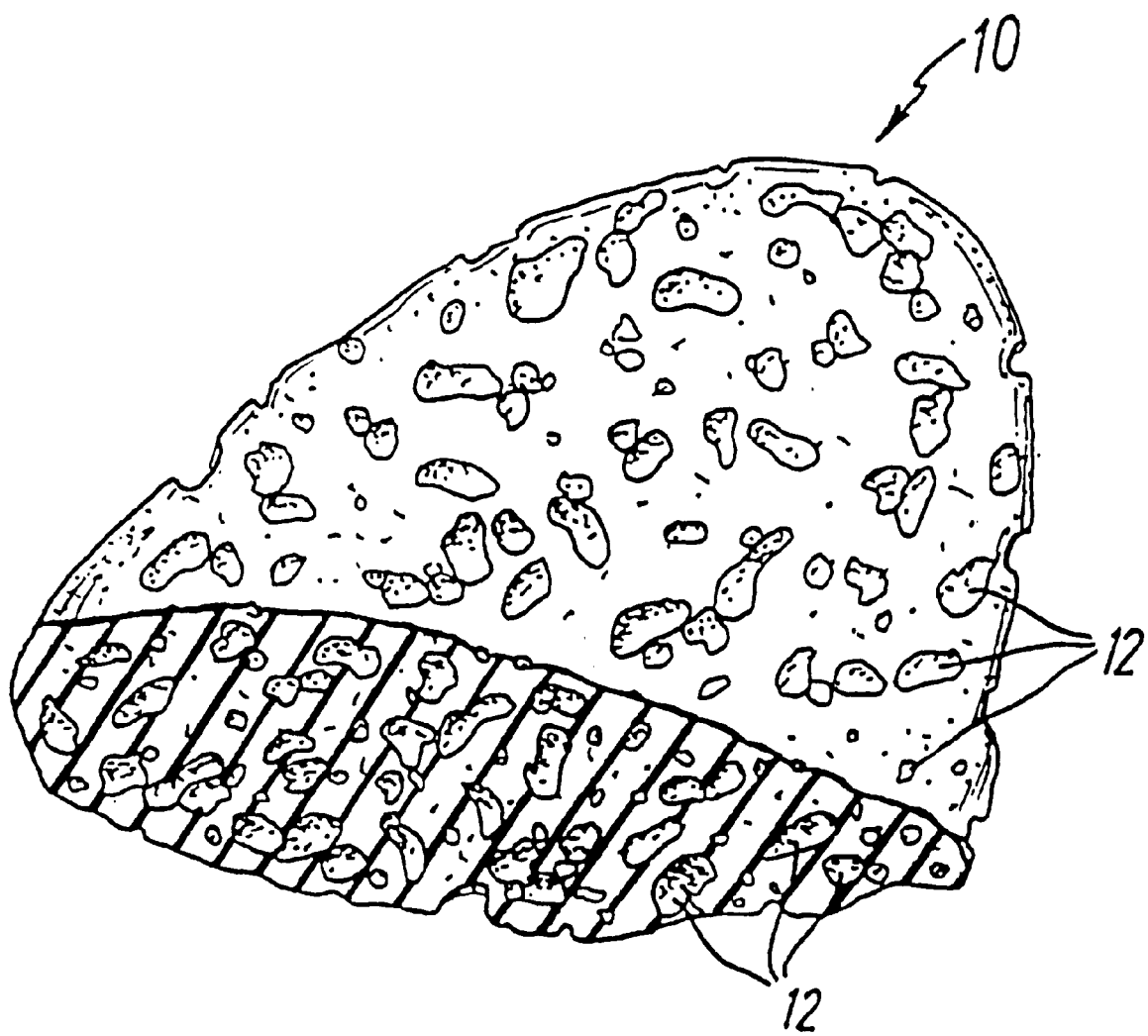

SILICONE RUBBER FOAM SUPPORT STRUCTURES FOR IMMOBILIZATION OF CELLS

This application is a national stage application, according to Chapter II of the Patent Cooperation Treaty. This application claims the priority date of Dec. 31, 1992 for U.K. Patent Application No. 9227134.5.

TECHNICAL FIELD AND BACKGROUND OF THE INVENTION

The present invention relates to cell support structures, particularly but riot exclusively to cell support structures for immobilizing cells.

The immobilization of biological cells by loading them onto a support structure is a technique often used by scientists in the production of important biologically derived products. The technique offers numerous advantages over free cell, liquid phase systems, including permitting increased ease of separation of the cells from the reaction medium, increased throughput flow rates in continuous reaction systems, increased cell density per unit volume of reaction medium, and the production of a relatively cell-free, product containing medium which in turn facilitates downstream processing.

Conventional immobilization materials suffer from several disadvantages. Some materials, such as synthetic polymers are relatively expensive and harmful, often causing a decrease in cell viability and/or product activity. Other materials used such as Agar, are mechanically soft, unstable and also cause cell viability problems. Calcium Alginate is currently one of the more popular materials used, but suffers from being relatively unstable and mechanically weak, and thereby prone to structural collapse during use, and is also susceptible to chemical attack.

SUMMARY OF THE INVENTION

It is an object of the present invention to obviate or mitigate these disadvantages.

According to the present invention there is provided a resilient cell support structure comprising silicon or a derivative thereof.

The structure may be of any suitable configuration, for instance beads, blocks, sheets, pads, chips, strands, tubes or granules. The structure may be formed or adapted to be locatable in or around and/or connectable to other component(s), for instance a reaction vessel or the like.

Preferably the structure is porous, for instance, the structure may be a sponge or foam. The porosity and/or density of the structure is preferably controlled according to the intended application. The porosity and/or density may be engineered by adding one or more additives to the structure, preferably substantially inert additives. Metal powder, such as stainless steel powder may be added to provide a relatively dense structure. Alternatively or additionally the porosity and/or density may be engineered by controlling aeration of liquid structure material during manufacture of the structure.

Preferably one or more substances may be added to give the structure particular surface properties. The or at least one of the substances may cooperate with biological cells.

Preferably the structure comprises silicone rubber.

Preferably the structure is re-usable.

The invention also provides a method of immobilizing cells the method comprising introducing a cell or cells to a resilient support structure comprising silicon or a derivative thereof.

The structure used may be of any suitable configuration, for instance block, sheet, pad, chip, strand, tube or granule. The structure may be formed or adapted to be locatable in or around and/or connectable to other component(s), for instance a reaction vessel or the like.

Preferably a culture of cells is grown on the support structure, preferably in conditions favouring growth. A plurality of cell cultures of different types of cells may be grown on a support structure.

Preferably the cells are introduced and/or grown on a porous structure, preferably in favourable conditions of acidity or alkalinity. The structure may be a sponge or foam. The growth conditions may be controlled to enable the extent of colonisation of the structure by the cells to be controlled.

The porosity and/or density of the structure is preferably controlled according to the intended application. The porosity and/or density may be engineered by incorporating one or more additives to the structure, preferably inert additives. Metal powder such as stainless steel powder may be added to provide a relatively dense structure. Alternatively or additionally the porosity and/or density may be engineered by controlling aeration of liquid structure material during manufacture of the structure.

Preferably one or more substances may be added to give the structure particular surface properties. The or at least one of the substances may cooperate with biological cells.

Preferably the cell(s) are introduced to a structure of silicone rubber.

Preferably the structure is sterilised before use. Preferably the structure is re-usable, and may be resterlised for re-use, once the desired reaction is complete.

According to a further aspect of the present invention there is provided a reaction system comprising a resilient cell support structure comprising silicon or a derivative thereof located within a reaction medium comprising a reactant, the support structure having cells located thereon in use, to enable or facilitate the desired reaction. The structure may have any of the features set forth above.

BRIEF DESCRIPTION OF THE DRAWINGS

An embodiment of the present invention will now be described by way of example only, with reference to the accompanying drawing which is a diagrammatic representation of a cross-section through a cell support structure according to the present invention.

DETAILED DESCRIPTION OF THE INVENTION

A cell support structure 10 for immobilizing biological cells, comprises silicone foam rubber. The structure 10 may be in any form convenient for the particulular intended use, for example granular (see drawing), sheet, bead, tube, chip, strand, pad or block form.

The structure 10 may also be formed or shaped to locate on or in or to connect to any other component of a reaction system in which it is to be used, for instance the or each structure may be shaped for assembly into the structure of a bioreactor.

During manufacture of the structure 10, if it is desirable, the porosity and/or density of the resultant structure 10 can be engineered. This may be done by selectively setting the environmental conditions of manufacture and/or incorporating inert additives into the structure 10. For instance dense particles such as stainless steel powder may be added to produce relatively dense structures. Alternatively, or in addition, the porosity may be increased (and density decreased) by increasing aeration of the liquid rubber during manufacture of the structures 10. This is important, since where the cells to be used are relatively large, then it is desirable to produce a structure 10 with relatively large pores 12, to accommodate the cells. In contrast when immobilizing cells that are relatively small, it is desirable to use a structure having pores 12 of relatively small size, thus maximizing the available surface area within the structure 10 to which the cells can attach. If the pores 12 are unduly large, then there will be considerable stacking of cells on the available surfaces. This stacking prevents cells cloaked by other cells from interacting with the reaction mixture efficiently. What is more, the available reaction surface will be relatively small. These conditions provide for poor efficiency.

The density is preferably increased as above when the reaction produces gases or otherwise involves gases, which aerate the reaction mixture and would tend to increase the buoyancy of the structure 10 through the adherence of bubbles to the structure 10. Increasing the density as necessary will ensure that the structures 10 and cells attached thereto remain in the reaction mixture to give maximum reaction exposure, and not allow them to float to and remain on the surface of the reaction mixture where the cells will not be involved satisfactorily in the desired reaction. This is relevant to fermentation reactions, where significant volumes of carbon dioxide are often produced.

As mentioned, the structures 10 are intended primarily for use in reaction systems comprising biological cells (Bioreactors) to immobilize the cells.

The immobilized cells are physically confined or localised on the surfaces of the structure 10, including surfaces defining pores within the structure 10. The structure 10 may be manufactured to comprise agents on the surface thereof which facilitate retention of the cells and/or the desired reaction. The cells retain their catalytic properties, preferably along with their viability, and can be used repeatedly and continuously. It is to be appreciated that there may be some leakage of cells from the structure 10. This leakage may or may not be significant, depending upon the particular reaction involved. It is possible to use the structures 10 as a means of feeding cells into a reaction medium, in particular reaction conditions.

The silicone structure 10 immobilizes the cells by adsorbing the cells onto its surfaces, which are inert. It may be termed a "natural" immobilization since the cells have a natural tendency to coat the surfaces and line the pores 12 of the structure, enabling maximum cell biomass to be loaded onto the structures 10. This in turn allows for maximum biocatalytic activity. However the efficiency of this form of immobilization is found to be affected by the environmental conditions, and often an optimum value for various factors such as acidity and alkalinity must be found in order to maximise the adsorption of the cells on to the support structure 10. Adsorption immobilization has the advantage of being very gentle and passive enabling cells to generally retain their viability.

Thus, a culture of the relevant cells is first grown on sterile support structures 10 in conditions for optimum growth (which may be different from the normal operating conditions in the bioreactor). The resilient nature of the structures 10 permits considerable cell loading, without collapse or disintegration of the structure 10. The foam nature of the structure 10 increases the surface area available for colonisation, per unit volume of material. It is to be appreciated that the density of colonisation (loading) of the structures 10 can be predetermined by setting the growth conditions. For example, one essential nutrient or condition may be limiting. Furthermore, it is also possible, if desired, to grow cultures of different cells on the structures 10. Once the culture 10 has been grown to the desired density on the support structure 10, the cell-loaded structures 10 can be introduced to the reaction medium, which may be in a bioreactor as will be described.

Thus, in use, cell-loaded structures 10 are introduced into the reaction medium containing the ingredients necessary for the cells to perform and produce the desired product(s). The conditions within the bioreactor may be different to those in which the structure 10 was loaded. The bioreactor conditions are then maintained to allow the cells to react with the surrounding medium to produce the required products.

Once the reaction is complete, then the cell-loaded structures 10 may be filtered, gently centrifuged or otherwise simply removed from the reaction medium, which now contains the desired product. Simple filtering techniques are sufficient to leave a relatively cell free, product-containing medium. The product-containing medium may contain some free cells leaked from the structures 10 which may be removed using further purification techniques if desired. The product can then be isolated from the medium using conventional techniques.

The support structures 10 can be re-used. They can be cleaned of cells by using a variety of conventional techniques, including chemical and mechanical cleaning. Alternatively, the cells may be allowed to remain, for re-use. The robust, durable and resilient properties of the silicone rubber foam enable it to withstand pressures from high cell packing within the pores, shear and impact with moving objects, for example an impeller which may be employed during the reaction. The structures 10 can be mechanically filtered out of the product-containing medium, under pressure if necessary, without harm. The structures 10 can be cleaned in steam, for example super-heated steam (126° C.) for an hour or more, and are also resistant to deterioration in an autoclave. Chemical cleaning can also be employed, including solvents such as ethanol, acid bleaching and suitable acid or alkali cleaning liquids can be used without detriment. This enables the support structures 10 to be effectively and efficiently cleaned to a condition for re-use.

The non-contaminating and inert nature of the support structures 10 enables them to be used in the production of proteins and other materials for use in the treatment of human and animal bodies, for example, in the production of proteins such as somatastatin, human growth hormone etc. The structures 10 are also particularly useful for purifying liquids, for instance water. Loaded structures 10 can be introduced into contaminated water. The cells, chosen according to a particular application, take-up the contaminants, reduce them to a non- or less-hazardous material, or otherwise remove or reduce the contamination, to leave purified or part purified water. This is particularly useful in the treatment of sewage waste. The structures 10 are also expected to be useful in the fermentation industry, allowing yeast cells to be attached to the structures 10 throughout the fermentation process and removed with the structures 10, so that the conventional problems associated with clouding of the fermentation mixture are obviated or mitigated.

It has been found that the silicone structure is non-toxic to and biocompatible with living cells, and also tends to encourage cell adhesion to, and colonisation of, the pore surfaces of the structure 10. Experiment has shown that brewing yeast, Saccharomyces cerevisiae, enjoys the above benefits, which indicate that both bacteria and moulds, as well as plant and animal cells are expected to be efficiently immobilizable on the structures 10.

The resilient nature of the structure 10 also enables substantial accumulation of cells, without disintegration of the structure 10. This has been a particularly notable disadvantage in conventional systems. Furthermore, the silicone structure does not appear to inhibit cell action, or function.

Whilst endeavouring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

We claim:

1. A method of immobilizing cells for cell growth and the production of cellular products, said method comprising introducing at least one cell into an openly porous resilient support structure comprising, silicone rubber foam, said structure being formed prior to the introduction of the cells into the structure, the structure having surfaces which define open pores permitting the passage of fluids therethrough, and immobilizing said at least one cell on said surfaces that define open pores of the structure, said cells being adsorbed into said surfaces to permit retention of the cells by the structure.

2. The method according to claim 1, in which the structure is in the form of a block, sheet, strand, tube or granule.

3. The method according to claim 1 or 2, in which the structure forms part of a bioreactor structure.

4. The method according to claim 1, in which a culture of cells including said at least one cell is grown on said surfaces that define open pores of the support structure.

5. The method according to claim 4, in which said culture of cells is exposed to conditions which enable growth.

6. The method according to claims 4 or 5, in which a plurality of cell cultures are grown on said surfaces that define open pores of the support structure.

7. The method according to claim 5, in which the cells are exposed to conditions of acidity or alkalinity which enable growth.

8. The method according to claim 7, in which porosity of the structure is controlled.

9. The method according to claim 8, in which the porosity is provided by incorporating at least one additive with silicone rubber during formation of the structure.

10. The method according to claim 1, wherein the structure has a density which substantially prevents the structure from floating in a reaction mixture with which the structure is to be used.

11. The method according to claim 10, in which the density of the structure is provided by incorporating at least one additive with silicone rubber during formation of the structure.

12. The method according to claim 9 or 11 in which the at least one additive is substantially inert.

13. The method according to claim 12, in which the at least one additive comprises metal powder.

14. The method according to claim 13, in which the at least one additive is stainless steel powder.

15. The method according to claim 1, in which the structure is formed from liquid silicone rubber which is aerated during formation of the structure to produce the silicone rubber foam, and porosity and density of the structure are provided by controlling the aeration of liquid silicone rubber during manufacture of the structure.

16. The method according to claim 15, in which a substance is added to the liquid silicone rubber to give the structure desired surface properties.

17. The method according to claim 1, in which the structure is sterilized before use.

18. The method according to claim 1, in which the structure is re-usable.

19. The method according to claim 18, in which the structure can be re-sterilized for re-use.

20. An openly porous resilient cell support structure having surfaces defining open pores permitting the passage of fluids therethrough and for containing cells immobilized thereon, the support structure comprising a silicone rubber foam having cells located on said surfaces that define pores of the structure, said cells being adsorbed into said surfaces to permit retention of the cells by the structure, and said structure being located within a medium for cell growth or a medium for the production of cellular products.

21. The structure according to claim 20, in which the structure is in the form of beads, blocks, sheets, strands, tubes or granules.

22. The structure according to claim 20 or 21, in which the structure forms part of a bioreactor structure.

23. The structure according to claim 20, in which porosity of the structure is controlled.

24. The structure according to claim 23, in which the porosity is controlled by including at least one additive in silicone rubber during formation of the structure.

25. The structure according to claim 24, wherein the structure has a density which substantially prevents the structure from floating in a reaction mixture with which the structure is to be used.

26. The structure according to claim 25, in which the density is provided by including at least one additive as a constituent of the structure.

27. The structure according to claim 26, in which the at least one additive is substantially inert.

28. The structure according to claim 27, in which the additive is metal powder.

29. The structure according to claim 28, in which the metal powder is stainless steel powder.

30. The structure according to claim 20, in which the structure is formed from liquid silicone rubber which is aerated during formation of the structure to produce the silicone rubber foam, and porosity and density are provided by controlling the aeration of the liquid silicone rubber during manufacture of the structure.

31. The structure according to claim 20, in which a substance is included as a constituent of the structure to modify surface properties of the structure.

32. The structure according to claim 20, in which the structure is re-usable.

33. The structure according to claim 20 in which the structure forms part of a bioreactor structure.

\* \* \* \* \*